United States Patent [19]

Rutger et al.

[11] 4,351,130
[45] Sep. 28, 1982

[54] RECESSIVE TALL—A FOURTH GENETIC ELEMENT TO FACILITATE HYBRID CEREAL PRODUCTION

[75] Inventors: J. Neil Rutger, Davis; Howard L. Carnahan, Biggs, both of Calif.

[73] Assignee: The United States of America as represented by the Secretary of Agriculture, Washington, D.C.

[21] Appl. No.: 274,087

[22] Filed: Jun. 16, 1981

[51] Int. Cl.³ ............................................. A01G 1/00
[52] U.S. Cl. .................................. 47/58; 47/DIG. 1
[58] Field of Search ............................ 47/58, DIG. 1

[56] References Cited

U.S. PATENT DOCUMENTS 4,051,629 10/1977 Galinat .................................... 47/58
4,143,486 3/1979 Maan ....................................... 47/58

Primary Examiner—Robert E. Bagwill
Attorney, Agent, or Firm—M. Howard Silverstein; David G. McConnell; Margaret A. Connor

[57] ABSTRACT

A recessive gene for tallness in plants is used as the fourth genetic element along with cytoplasmic-genetic male sterility, sterility maintainers and fertility restorers to facilitate hybrid seed production. The recessive tall gene is incorporated into the pollen fertility restoring parent (R-line) in hybrid seed production crosses (A-line × R-line crosses).

10 Claims, 8 Drawing Figures

RECESSIVE TALL—A FOURTH GENETIC ELEMENT TO FACILITATE HYBRID CEREAL PRODUCTION

FIELD OF THE INVENTION

This invention relates to the breeding of cereal crop plants. In particular, it relates to producing hybrid seeds for commercial use.

DESCRIPTION OF THE PRIOR ART

Methods of using genetic techniques to facilitate production of hybrid seed corn were outlined in U.S. Pat. No. 2,753,663 ('663) which is hereby incorporated by reference. While not explicitly referred to as "genetic elements," the methods in '663 depended upon use of three such elements: cytoplasmic-genetic male sterility, sterility maintainers, and fertility restorers. These three genetic elements have also been used in production of hybrid seeds of sorghum, wheat, pearl millet, and probably other grain crops as well. For further details of the use of these genetic elements, see *Principles of Plant Breeding* by R. W. Allard, John Wiley & Sons, Inc., New York, New York, (1960), pp. 243–251 and 465–472; Choyu Shinjyo, *Sci. Bull. Coll. Agr. Univ., Ryukuys*, No. 22: 1–57 (1975); and U.S. Pat. No. 3,710,511, which are hereby incorporated by reference.

The three-element method works as follows:

a. As shown in FIG. 1, plants having cytoplasmic-genetic male sterility are produced as follows: A source of male sterile cytoplasm (cms) is introduced into a desired parent line (designated the B-line, with normal (n) cytoplasm) by repeated backcrossing, using the cytoplasmic male sterile lines with non-fertility-restoring genes (rf) as the female and the desired parent (B-line) with normal cytoplasm(n) and nonfertility-restoring genes (rf) for sterile cytoplasms as the recurrent male parent. The B-line is male fertile, because the fertility-restoring genes are not needed for its normal cytoplasm. The recovered male sterile line is designated the A-line. "A" lines are cytoplasmic male sterile lines used in hybrid seed production. The A-line is very similar agronomically and genetically to the original B-line, except that the A-line has a male sterile cytoplasm (cms) while the original B-line has normal (n) cytoplasm.

b. A diagram depicting sterility maintainers is shown in FIG. 2. Sterility maintainers are called "B" lines in hybrid seed production. The male sterile A-line is maintained by pollination from the B-line which has normal cytoplasm (male fertile) and non-fertility restoring genes. The B-line is maintained by self pollination. This process produces more A-line seed.

c. Fertility is restored to the A-line as follows (FIG. 3). The male sterile A-line (cms-rfrf) is crossed with the male fertile, fertility-restoring R-line to produce hybrid seed. The seed from the A×R hybrid is sold to the farmer for growing hybrid plants. The hybrid plants grown by the farmer will be male fertile.

A major limitation is the successful use of the above three elements in wheat, rice and other naturally self-pollinating plants is insufficient pollen dispersal to economically produce hybrid seed. In parents of similar height, wind dispersal is inefficient. Hand pollination techniques to disperse pollen are labor intensive and costly.

SUMMARY OF THE INVENTION

The invention described herein provides means for obviating the above problems. The invention consists of a method of using a recessively-inherited tall plant as a male pollinator in crosses with short statured female plants. Since this tall plant is recessively inherited, the $F_1$ hybrid produced by such a cross is short, like the short female parent. The recessively-inherited tall plant type is an exception to the general case in which tall plant type is dominant to short plant type.

In accordance with the invention, a recessive gene for tallness in plants is incorporated as the fourth genetic element—the other three genetic elements being cytoplasmic-genetic male sterility, maintainers, and restorers—to facilitate hybrid seed production in cereals. The recessive tall gene is incorporated into the pollen fertility restoring parent (R-line) in hybrid seed production crosses (A-line×R-line crosses).

An important advantage of the use of a recessively-inherited tall plant to pollinate short plants is that wind dispersal of pollen from the tall plant onto the short one would be sufficient to maximize the crossing and produce hybrid seed. Expensive hand labor is thus eliminated.

Another advantage of the invention is that in crosses with semidwarf female plants, the resulting hybrid plants would be semidwarf, unlike the usual case of tall hybrids from semidwarf by tall crosses. This becomes important in cases in which the semidwarf plant type is known to be more productive than the tall plant type, such as in the case of many cereals.

Another advantage of the invention is that the increased height of one parent permits a co-mingling of the hybrid parent seed stocks to maximize crossing and facilitates mechanical removal of the paternal parent before mass harvest of the commercial hybrid seed.

BRIEF DESCRIPTION OF THE DRAWINGS

FIG. 1 depicts steps for the production of cytoplasmic male sterile plants (A-line).

FIG. 2 depicts the step for maintaining male sterility in plants.

FIG. 3 depicts the step of restoring fertility to produce hybrid seed.

DETAILED DESCRIPTION OF THE INVENTION

The first step is obtaining plants having recessive tall genes (rt) is inspecting a plant crop and selecting plants which are taller than the others (i.e., those plants which are taller than plants having dominant genes for shorter stature (Rt)). Such tall plants could originate through: (a) mechanical mixture, that is, the seeds having tall characteristics were inadvertently mixed with the other seeds; (b) outcrossing with a tall variety, that is, the tall plants resulted from pollination of recessive short females by dominant tall males; (c) genetic recombination between normal plants, (d) spontaneous mutation, or (e) induced mutation, that is, mutation caused by radiation, chemicals, or the like.

Next, each tall plant is crossed with the shorter plant variety. The $F_1$ generation of each cross is grown and the rare $F_1$ that is short like the short parent is selected. Next, the $F_2$ generation of those crosses which gave the short $F_1$'s are grown. If the expected segregation of 3 short:1 tall occurs, this is proof that a recessive tall has been found.

Since this recessive tall gene will be used as the male parent or pollinator or R-line, it must be sufficiently taller than the female plant to allow pollen from the male plants to be efficiently dispersed onto the female plants by wind and gravity to pollinate the female plants. (Where the male parent is close enough to the female to allow dispersal of pollen onto the female, the plants are said to be in "pollinating proximity.")

Figure 1:
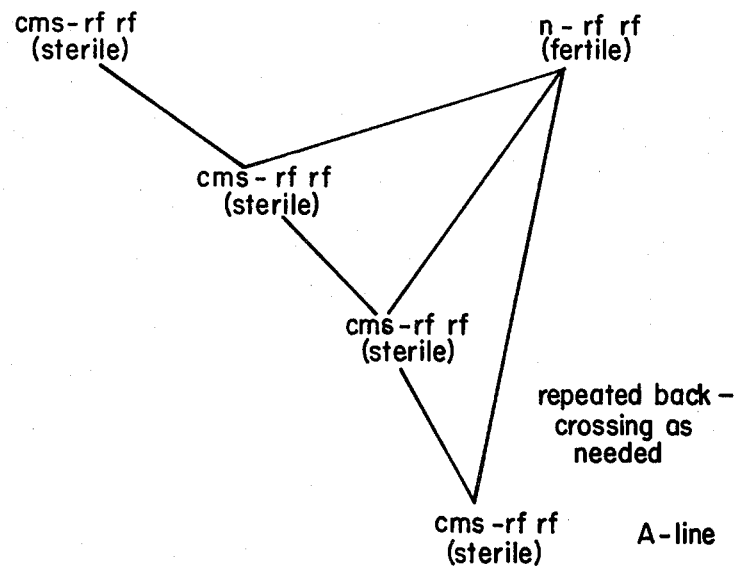
FIGS. 1–3 depict what is known in the prior art.
Figure 2:
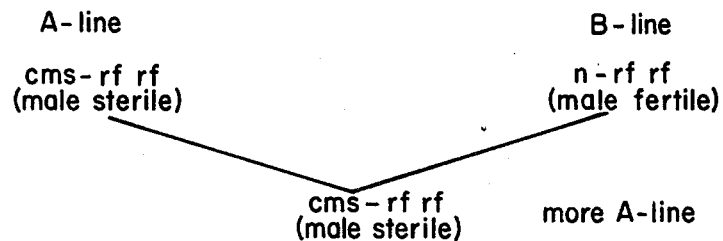
Figure 3:
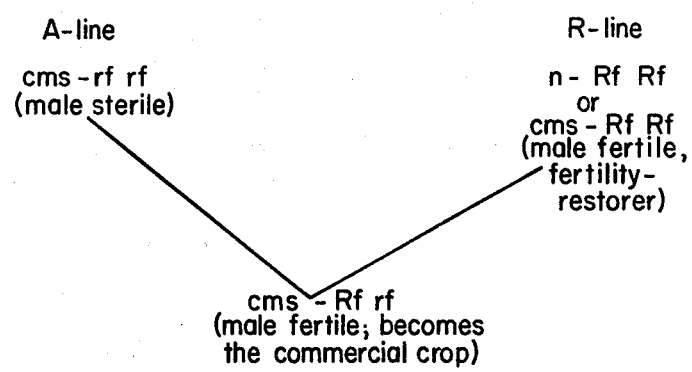
Figure 4:
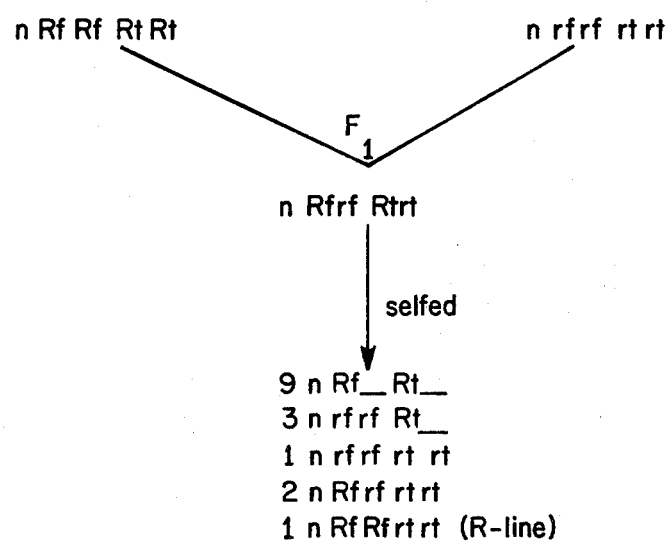
FIG. 4 depicts the method of recombining the fertility restoring genes (RF) and the recessive tall genes (rt) into the fertility restoring, recessive tall parent.

If the plant having the recessive tall gene does not have a fertility restoring gene (RF), the latter is incorporated therein as shown in FIG. 4. The recessive tall (rt), non-fertility restoring (rf) male parent plant having normal cytoplasm is crossed with a short (Rt), fertility restoring (Rf) female having normal cytoplasm. The $F_1$ generation (n-Rfrf Rtrt) is selfed. The tall $F_2$ progeny from selfing of the $F_1$ generation is test crossed with a cytoplasmic male sterile (cms) non-fertility restoring (rf) short (Rt) female plant. The $F_2$ generation plant whose test cross progeny are all fertile short plants is the desired normal cytoplasmic, fertility restoring, recessive tall (n RfRf rtrt). This is the R-line which is crossed with an A-line to produce hybrid seed in the manner of the invention. The invention is useful in hybridization of plants such as cereal grains in which the height differential would be an advantage. The important cereal grains include wheat, oats, rice, corn, rye and the like.

This height differential provides means for efficient wind dispersal to maximize crossing and produce hybrid seed. The increased height of the pollinator parent maximizes pollen dispersal by wind and gravity on to the shorter maternal parent. Incorporation of this element overcomes the major limitation of sufficient pollen dispersal in the successful use of the other three elements in plants to ensure economic production of hybrid seed.

The invention is particularly useful where the A-line is a semidwarf plant type which is more productive than the tall variety. The semidwarf plant type has been an integral part of the world's "Green Revolution," and is a component of most modern cereal breeding programs. Other plants useful in the invention will be recognized by those skilled in the art.

The invention will next be illustrated by but not limited to the production of hybrid semidwarf rice seed.

A rice plant having a recessive gene for tallness was developed as follows: semidwarf 'M9' rice (a well known semidwarf rice variety having two alleles of the recessive semidwarfing gene ($sd_1$ $sd_1$) and which derived semidwarfism from 'IR8' (a well known short stature vvariety ($sd_1$ $sd_1$) were crossed with 'Terso' (a proprietary tall rice variety ($Sd_1$ $Sd_1$)). Several plants having very long upper internode were discovered in the $F_3$ generation and one plant with elongated internode, designated 76:4512 ($P_1$), was selected. Seeds from 76:4512 ($P_1$) identified as C.I. 11055 have been deposited in the Germ Plasm Resource Laboratory, USDA, SEA, AR, NER, BARC-West, Bldg. 047, Beltsville, Md. Genetic studies indicated that tallness was controlled by a single recessive gene. The gene symbol eui was proposed for this elongated uppermost internode character to designate the recessive tall (rt) characteristic.

The R-line containing the eui gene is obtained from 76:4512 ($P_1$) as previously described (FIG. 4).

Figure 5:
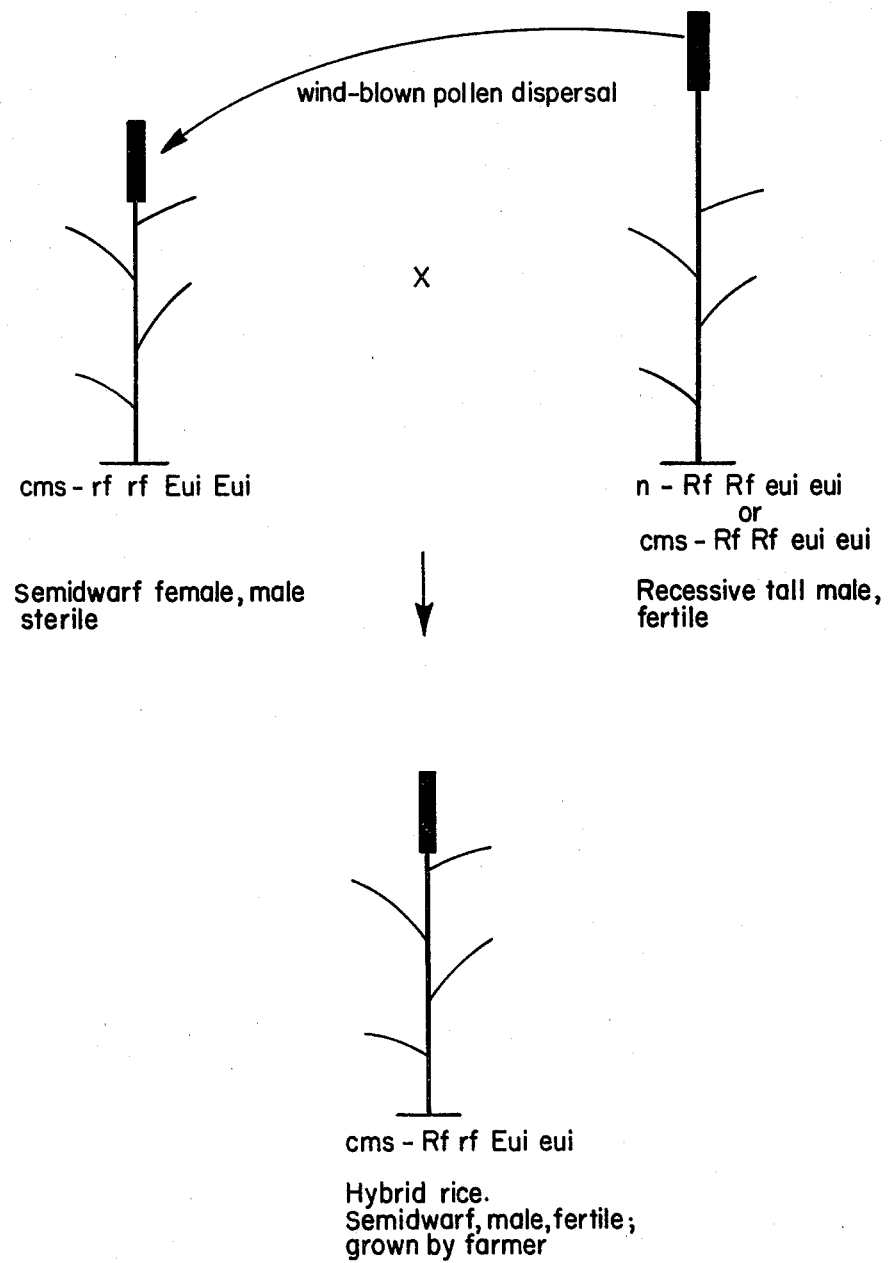
FIG. 5 depicts use of the recessive tall plant type (eui eui) as the fertility-restoring male parent in the cytoplasmic male sterile×restorer technique of hybrid seed production.

In one embodiment of the invention, the recessive gene for elongated internode (eui) is incorporated into the restorer parent of hybrid rice as described above. Then this parent (R-line) is interplanted with the male sterile seed parent (A-line) in commercial hybrid seed production fields (FIG. 5) to produce hybrid seed for use by farmers. Female and male parents are co-mingled, or in separate rows. As noted previously, tall male parents have an advantage in pollen dispersal in seed production fields. However, the tall $F_1$'s are normally dominant and result in tall cultivars. Such tall hybrids are unwanted in vast areas where semidwarf cultivars are known to be more productive than tall ones. In contrast, use of the present recessive eui gene in pollinator parents results in the desired short $F_1$ hybrids for the commercial crop.

Figure 6:
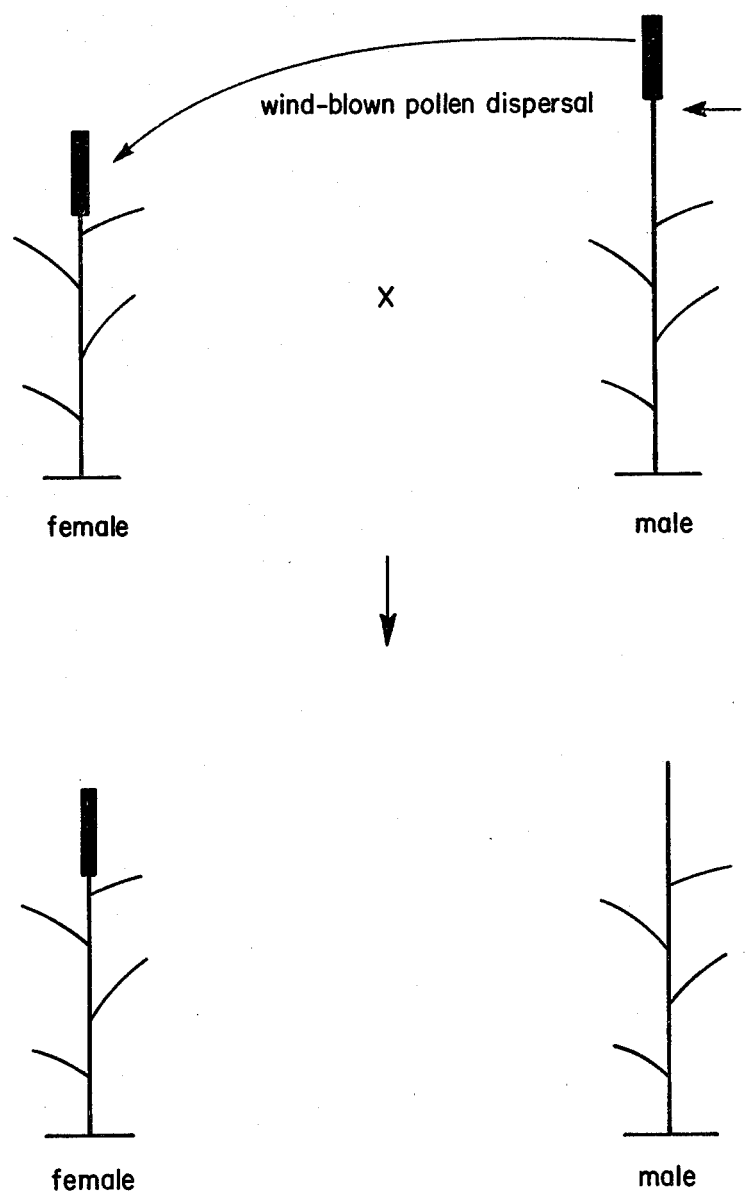
FIG. 6 depicts removal of male parent after pollination.

It is preferred that the pollinator is removed after pollination, so that the entire field may be harvested for hybrid seed production (FIG. 6). Female and male parents are comingled, or planted in separate rows. Since the pollinator is taller than the female parents, about 25 cm taller in the semidwarf rice variety containing the eui gene, the pollinators are effectively eliminated by clipping off their panicles, by rope-wick application of herbicide soon after pollination, or the like. After the pollinators are removed, the entire field is harvested for hybrid seed production, eliminating the need for separate harvest of female and male plants.

Figure 7:
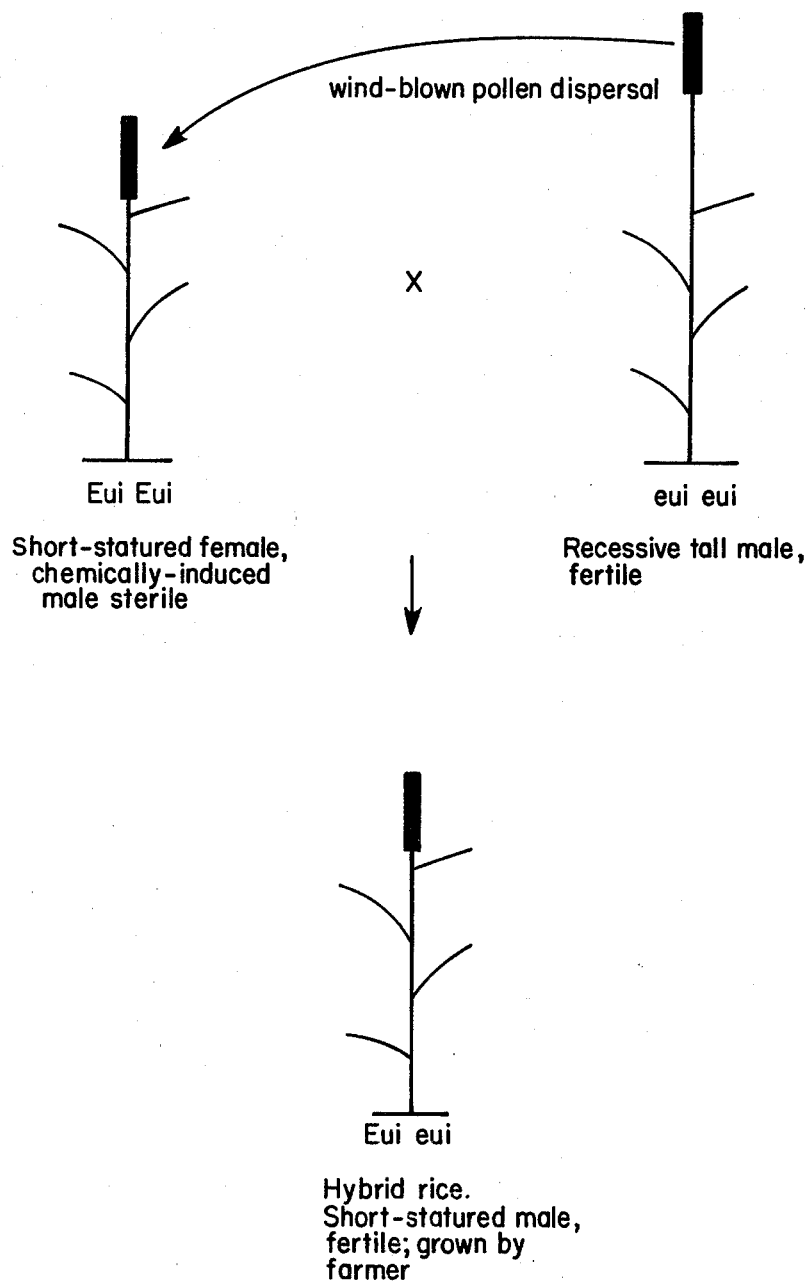
FIG. 7 depicts use of the recessive tall plant type (eui eui) as the male parent in the chemically-induced male sterile×normal male technique of hybrid seed production.

In another embodiment of the invention (FIG. 7), the recessive tall plant type (eui eui) is used as the male parent and fertile, short-statured plants are used instead of the usual "A" line as the parents in hybrid seed production. The tall and short parents are grown in separate rows. The rows chosen to be female are sprayed with a male sterility-inducing chemical, just prior to flowering.

Figure 8:
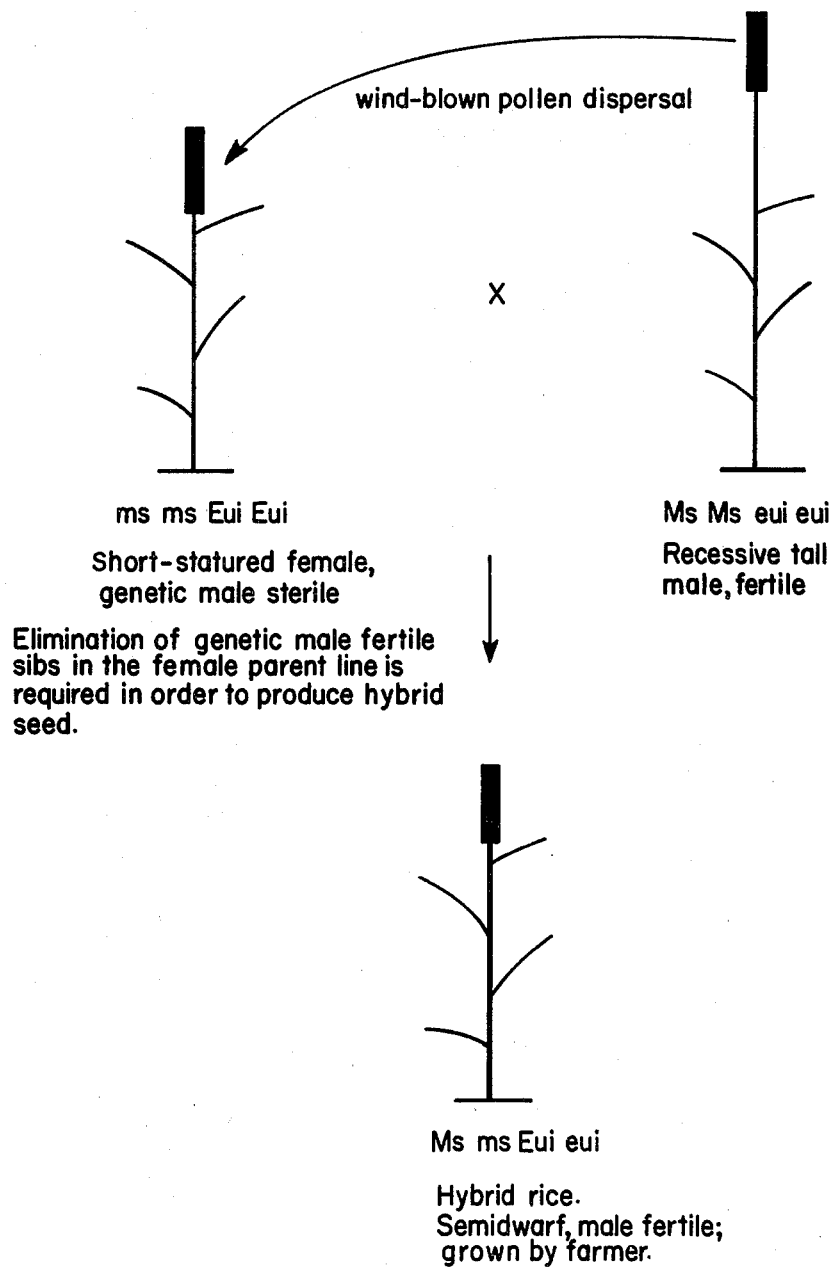
FIG. 8 depicts use of the recessive tall plant type (eui eui) as the male parent in the genetic male sterile×normal male technique of hybrid seed production.

In the embodiment shown in FIG. 8, the recessive tall plant type (eui eui) are used as the male parents and short-statured plants which are genetically male sterile (ms) are used as the female parents. Female and male plants are grown in separate rows. The genetic male fertile sibs in the female parent line are eliminated and hybrid rice is harvested.

What is claimed is:

1. A method of producing hybrid seed, comprising: growing together in pollinating proximity male pollinator plants which are characterized as recessively-inherited tall plant types having a recessive tall gene, and shorter female plants.

2. A method of producing hybrid seed, comprising: growing together in pollinating proximity male parent plants which have recessive tall genes and fertility restoring genes and female parent plants which have male sterile cytoplasm and non-fertility restoring genes; said male plants being sufficiently taller than said female plants to allow pollen from the male plants to be dispersed on to said female plants by wind and gravity to pollinate said plants and produce hybrid seed.

3. The method of claim 2 wherein said seed of said male and female parent plants are planted and harvested separately.

4. The method of claim 2 wherein said male pollinator plants are effectively eliminated after pollination.

5. The method of claim 2 wherein said female parent is a semidwarf plant variety.

6. A product produced in accordance with the method of claims 2, 3, 4 or 5.

7. A method of producing hybrid rice seed, comprising:

growing together in pollinating proximity recessive tall (eui) male parent rice plants which have fertility restoring genes and semidwarf female rice parent plants which have male sterile cytoplasm and non-fertility restoring genes to produce hybrid rice seed.

8. The method of claim 7 wherein said seed of said male and female parent rice plants are harvested separately.

9. A product produced by said female parent in accordance with the method of claim 8.

10. A recessive tall rice plant having elongated upper internode.

* * * * *